United States Patent [19]

Bailey

[11] Patent Number: 4,829,084
[45] Date of Patent: May 9, 1989

[54] METHOD FOR TREATING MALIGNANT CONDITIONS

[75] Inventor: Denis M. Bailey, East Greenbush, N.Y.

[73] Assignee: Sterling Drug Inc., New York, N.Y.

[21] Appl. No.: 226,599

[22] Filed: Aug. 1, 1988

Related U.S. Application Data

[63] Continuation-in-part of Ser. No. 129,631, Dec. 7, 1987, abandoned, which is a continuation of Ser. No. 537,197, Sep. 29, 1983, abandoned.

[51] Int. Cl.$^4$ .......................................... A61K 31/255
[52] U.S. Cl. ....................................................... 514/517
[58] Field of Search ................................. 514/517, 601

[56] References Cited

U.S. PATENT DOCUMENTS 2,917,432 12/1959 Timmis .................................... 167/65
3,997,585 12/1976 Hirsch ............................. 260/456 A
4,075,351 2/1978 Hirsch ................................. 424/303

FOREIGN PATENT DOCUMENTS 147540 7/1985 European Pat. Off. ............ 514/517

OTHER PUBLICATIONS

Hirsch et al., J. Med. Chem. 24, 901–903 (1981).

Primary Examiner—Jerome D. Goldberg
Attorney, Agent, or Firm—Thomas L. Johnson; Paul E. Dupont

[57] ABSTRACT

A method for inhibiting the growth of malignant cells in a mammal, said cells being susceptible to the action of a compound of the formula

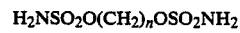

$$H_2NSO_2O(CH_2)_nOSO_2NH_2$$

where n is 6–8, which comprises administering to said mammal an antineoplastically effective amount of said compound incorporated in a suitable pharmaceutically acceptable excipient.

The compounds are particularly effective against malignant cells derived from or associated with leukemia, mammary tumors, melanoma or colon adenocarcinoma.

6 Claims, No Drawings

METHOD FOR TREATING MALIGNANT CONDITIONS

This application is a continuation-in-part of copending application Ser. No. 129,631, filed Dec. 7, 1987, now abandoned, which is in turn a continuation of application Ser. No. 537,197, filed Sept. 29, 1983, now abandoned.

BACKGROUND OF THE INVENTION (1) Field of the Invention

The present invention relates to a method for treating malignant conditions in mammals by administration of sulfamate compounds.

(2) Information Disclosure Statement (a) Prior Art

Hirsch U.S. Pat. Nos. 3,997,585 (Dec. 14, 1976) and No. 4,075,351 (Feb. 21, 1978), and Hirsch et al., J. Med. Chem. 24, 901–903 (1981), describe a series of sulfamate compounds having male antifertility properties. The compounds have the formula

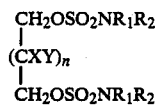

wherein n is an integer from 0 to 8 and X and Y are hydrogen, provided that when n is 1, X and Y are hydrogen, lower alkyl having 1-3 carbon atoms, phenyl, benzyl or phenethyl; $R_1$ and $R_2$ are hydrogen, alkyl having 1-7 carbon atoms, phenyl, benzyl, phenethyl or cycloalkyl having 5-6 carbon atoms. Compounds specifically disclosed include 1,6-bis-O-sulfamyl-1,6-hexanediol, 1,7-bis-O-sulfamyl-1,7-heptanediol, and 1,8-bis-O-sulfamyl-1,8-octanediol.

Timmis U.S. Pat. No. 2,917,432, issued Dec. 15, 1959 discloses a process for producing remissions in patients suffering from chronic myeloid leukemia which comprises administering 1,4-dimethanesulfonyloxybutane to a patient afflicted with the disease. This compound has the formula

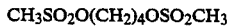

and is known commercially under the generic name busulfan.

(b) Publication Subsequent to Filing Date of Application Ser. No. 537,197

Sterling Drug Inc. European Patent Application No. 84111578.5 was published July 10, 1985 under Publication No. 147,540 with a disclosure identical with that of U.S. patent application Ser. No. 537,197, filed Sept. 29, 1983.

SUMMARY OF THE INVENTION

The inventive concept resides in a method for inhibiting the growth of malignnant cells in a mammal, said cells being susceptible to the action of a compound of the formula

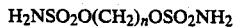

where n is 6-8, which comprises administering to said mammal an antineoplastically effective amount of said compound incorporated in a suitable pharmaceutically acceptable excipient.

The compounds are particularly effective against malignant cells derived from or associated with leukemia, mammary tumors, melanoma or colon adenocarcinoma.

DETAILED DESCRIPTION INCLUSIVE OF PREFERRED EMBODIMENTS

Unexpectedly, it has been found that a series of alkanediol disulfamates, disclosed in the prior art as having male antifertility activity, possess antineoplastic activity as evidenced by their activity in reducing the size of tumors and increasing the survival time in murine species implanted with various tumors.

The antitumor activity lies essentially in homologs of the formula

where n is 6-8, inclusive.

The alkanediol disulfamates were prepared according to the prior art method by reacting an alkanediol with sulfamoyl chloride in the presence of sodium hydride, as illustrated by the following procedure:

A 57% oil dispersion of sodium hydride (11.8 g, 0.28 mole NaH) was added to 150 ml of tetrahydrofuran. The suspension was stirred and gently heated, and 15.84 g (0.12 mole) of 1,7-heptanediol in 75 ml of tetrahydrofuran was added gradually over a period of 90 minutes. An additional 25 ml of tetrahydrofuran was then added, and the reaction mixture was stirred at reflux for five hours. An additional 150 ml of tetrahydrofuran was added, and to the stirred warm mixture there was added dropwise a solution of 28.9 g (0.25 mole) of sulfamoyl chloride in 150 ml of tetrahydrofuran over a two hour period. The reaction mixture was stirred at reflux for five hours, then cooled and treaated dropwise with 125 ml of water. The mixture was acidified with 2N hydrochloric acid, and the organic layer was separated and dried over anhydrous sodium sulfate. The solvent was removed in vacuo and the residue triturated with ethyl acetate to give a yellow solid which was recrystallized from an ethyl acetate—hexane mixture to give 22.0 g of 1,7-heptanediol disulfamate as colorless granules, m.p. 87°–88° C.

By employing the same procedure but replacing the 1,7-heptanediol by a molar equivalent amount of 1,6-hexanediol or 1,8-heptanediol, there was obtained, respectively, 1,6-hexanediol disulfamate, colorless granules, m.p. 122–124° C.; and 1,8-octanediol disulfamate, tan granules, m.p. 100°–101° C.

The compounds described hereinabove were tested for antitumor activity in mice under the auspices of the National Cancer Institute (U.S. Dept. of Health and Human Services) following the protocols set forth in *Cancer Chemotherapy Reports*, Part 3, Vol. 3, No. 2 (September 1972).

The compounds were tested against the following implanted tumors:

3B131=B1-B16 melanocarcinoma
3LE31=LE-L-1210 lymphoid leukemia
3MBG5=MB-MX-1 mammary carcinoma xenograft
3PS31=PS-P-388 lymphocytic leukemia
3CDJ2=CD-CD8F$_1$ mammary adenocarcinoma The results were determined at T/C (%) values, calculated in terms of mean survival rates (MST)

$$T/C\,(\%) = \frac{MST\text{ (treated animals)}}{MST\text{ (control animals)}} \times 100$$

or (for 3MBG5 and 3CDJ2) in terms of change in tumor weight according to the following procedures:

3MBG5: On day 0, tumor fragments with an average diameter of 9-12 ocular micrometer units (10 OMU=1 mm; weight of fragment with a length and width of 10 OMU=0.5 mg) are implanted beneath the renal capsule of athymic mice. On day 11, tumor measurements are taken again. All length (L) by width (W) measurements are converted to weight by the formula: wt. (mg)=(L'W×W)/2. For positive changes in test tumor weights (i.e. mean T.W. on day 11—mean T.W. on day 0 was positive), T/C values are calculated from the test tumor weight change/control tumor weight change×100. For negative changes in test tumor weights (tumors regressed), T/C values are calculated from the test tumor weight change/initial test tumor weight×100.

3CDJ2: On Staging day and final evaluation day, the sizes of tumors of individual mice are measured according to the following formula: Wt. (mg)=(L×W×W)/2. Change in tumor weight for each group is calculated. For positive changes in test tumor weights (i.e. median T.W. on final evaluation day—medium T.W. on Staging day), T/C values are calculated from the test tumor weight change/control tumor weight change×100. For negative changes in test tumor weights (tumors regressed), T/C values are calculated from the test tumor weight change/initial tumor weight×100.

The tables below give the results obtained with the compounds pertinent to the instant invention. The compounds were tested as suspensions in polysorbate 80 (Tween 80) and by intraperitoneal injection unless otherwise stated.

| | I 1,7-Heptanediol disulfamate | | |
|---|---|---|---|
| Tumor Systems | Dose (mg/kg/inj) | T/C (%) MST | Weight Change |
| 3B131 | 50 | 171-181 | |
| 3LE31 | 50 | 141-171 | |
| 3MBG5 | 150 | | −97 |
| 3MBG5 | 75 | | −81 |
| 3PS31 | 100 | 199 | |
| 3PS31 | 50 | 174 | |
| 3CDJ2 | 250 | | −27, −36 |

| | II 1,6-Hexanediol disulfamate | | |
|---|---|---|---|
| Tumor Systems | Dose (mg/kg/inj) | T/C (%) MST | Weight Change |
| 3B131 | 50 | 180 | |
| 3B131 | 25 | 168-185 | |
| 3LE31 | 24 | 158-178 | |
| 3MBG5 | 75[a] | | −24, −100 |
| 3PS31 | 100 | 294 | |
| 3PS31 | 50 | 193 | |

[a]subcutaneous administration

| | III 1,8-Octanediol disulfamate | | |
|---|---|---|---|
| Tumor Systems | Dose (mg/kg/inj) | T/C (%) MST | Weight Change |
| 3B131 | 25 | 132-140 | |
| 3LE31 | 50 | 186 | |
| 3LE31 | 25 | 146 | |
| 3MBG5 | 80[a] | | −87, −100 |
| 3PS31 | 50 | 174-179 | |
| 3CDJ2 | 250 | | −7 |
| 3CDJ2 | 125 | | 6 |

[a]subcutaneous administration

For practice of the invention, the compounds are prepared for use by incorporating them in conventional, pharmaceutically acceptable, diluents, carriers or excipients. For parenteral administration (intravenous, intraperitoneal, subcutaneous or intramuscular), the compounds are dissolved or suspended in an aqueous or non-aqueous vehicle. For oral administration, the compounds are formulated in dosage unit form as tablets or capsules. Exemplary diluents, carriers or excipients include lactose, dextrose, sucrose, sorbitol, mannitol, starches, gum acacia, calcium phosphate, mineral oil, cocoa butter, alginates, tragacanth, gelatin, methyl cellulose, methyl- and propyl hydroxybenzoates, talc, magnesium stearate and the like.

A preferred compound for use in the method of the invention is 1,7-heptanediol disulfamate. A new and improved method for its preparation is as follows.

A stirred solution of 12.91 kg of chlorosulfonyl isocyanate (ClSO$_2$NCO) in 29 L of methylene chloride was treated over one hour, under nitrogen, with a solution of 3.55 L of formic acid in 2.2 L of methylene chloride. A slight exotherm, 20° to 29° C., was encountered. The reaction mixture was stirred at ambient temperature for one-half hour, heated to reflux for 2½ hours and stirred at ambient temperature for one additional hour. The reaction mixture containing sulfamoyl chloride (ClSO$_2$NH$_2$) was cautiously treated over a 10 minute period with 7.79 kg of potassium carbonate and 3.05 kg of 1,7-heptanediol followed by heating at reflux for 2½ hours.

The reaction mixture was stirred at ambient temperature overnight and then diluted with 45 L of deionized water and 40 L of ethyl acetate. The layers were separated and the aqueous portion extracted with 2×20 L of ethyl acetate. The combined organic extracts were dried with 5.0 kg of magnesium sulfate and the drying agent was filtered through a filter cel pad and washed with 20 L of ethyl acetate. The filtrate was concentrated to dryness in vacuo and the solid residue was dissolved in 6.3 L of ethyl acetate and reprecipitated by adding 100.6 kg of methylene chloride. The suspension was cooled to −2° C. and the solids were collected and washed with 6.0 L of cold methylene chloride. Drying in vacuo at 40° C. afforded a total of 4.24 kg (67.0%) of crude product.

A solution of 5.49 kg of the crude product in 8.0 L of warm (60° C.) ethyl acetate was filtered through a filter cel pad on a sintered glass filter. After washing the filter cel pad with 3.0 L of hot ethyl acetate the filtrate and wash were charged to a 30 gallon kettle. The product was precipitated by the addition of 72.7 kg of methylene chloride over 30 minutes. After cooling it to 10° C. the solid was collected and washed with 8.0 L of methylene chloride followed by drying in vacuo at 40° C. to give 4.94 kg of 1,7-heptanediol disulfamate of 99.6% purity.

The animal testing data with respect to 1,7-heptanediol disulfamate (I) is summarized as follows.

The antitumor activity of I was initially identified in the ip implanted P388 leukemia prescreen. Following daily ip administration of a suspension of I in saline plus Tween 80 to tumor-bearing mice on days 1-5, maximum increases in life span (ILS) ranging from 52 to 130% (median 82%, mean 87%) were achieved. These effects were obtained with optimal doses ranging from 25 to 100 mg/kg/injection.

Following initial identification of its antitumor activity, I was evaluated against five mouse tumors and three human tumor xenografts. The compound demonstrated good activity against both the human and mouse mammary tumors. In the human MX-1 mammary tumor xenograft model, a 75 mg/kg dose administered on days 1, 5, 9 caused complete tumor regression in four of six mice. One half this optimal dose also was effective in reducing the size of the mammary tumors. In two additional experiments, complete tumor regressions were observed in nine of twelve mice treated with 150 mg/kg. I also caused regression of advance-stage mouse CD8F1 mammary carcinomas although no complete responses were achieved.

Three additional tumors that responded to treatment with I were the mouse B16 melanoma, L1210 leukemia and colon adenocarcinoma 38. In the tip implanted B16 melanoma model, optimal ILS values of 81 and 71% were obtained in two experiments following ip administration of a 50 mg/kg dose on days 1-9. With a dose of 25 mg/kg/injection, ILS values of 50% and 38% were achieved. The life spans of mice bearing the ip implanted L1210 leukemia were increased by 41-91% (mean % ILS for 4 experiments=64) following ip treatment with a daily dose of 50 mg/kg continued for nine days. With the same treatment route and schedule, I was slightly less effective against the sc implanted L1210 leukemia producing maximum ILS values of 45 to 79% in two experiments. Moderate activity was noted in two of three experiments using the sc implanted colon adenocarcinoma 38 model. Tumor growth was inhibited by 84 and 91% following ip administration of a 200 mg/kg dose on days 2 and 9.

In summary, I has demonstrated good activity in five tumor models (Table II): the ip implanted B16 melanoma, P388 leukemia and L1210 mammary tumor xenograft. Moderate to good activity has been observed in two additional models: the sc implanted colon adenocarcinoma 38 and L1210 leukemia. No activity has been observed against the iv implanted Lewis lung carcinoma or the src implanted human CX-1 colon and LX-1 lung tumor xenografts under the experimental conditions used.

The acute toxicity of I in mice was determined, single intravenous dose, with results as follows: $LD_{10}$ 138.8 mg/kg (416.4 mg/m$^2$), $LD_{50}$ 165.6 mg/kg (496.8 mg/m$^2$), $LD_{90}$ 197.5 mg/kg (592.5 mg/m$^2$). Based on a figure of one-tenth of the $LD_{10}$ dose, a starting dose of 42 mg/m$^2$ has been selected for clinical tests in humans by intravenous administration. In the absence of toxicity the dose level will be increased incrementally to doses as high as 462 mg/m$^2$, or until significant toxicity is observed.

A preferred formulation containing I is prepared as follows: I (300 mg) is freeze-dried from t-butyl alcohol in a 10 ml flint vial. The resulting material is dissolved in 9.6 ml of a vehicle composed of 10% ethanol, 40% propylene glycol and 0.05M, pH 7.4 phosphate buffer, qs, to yield a 30 mg/ml solution of I. For intravenous administration, the solution of I is placed in 150 ml of normal saline for infusion over a period of 30 minutes.

Studies by the National Cancer Institute have demonstrated that the standardized tests using the animal tumor systems described hereinabove are highly predictive of clinal results in humans against the corresponding tumors, as reported by J. M. Venditti in Pharmacological Basis of Cancer Chemotherapy (Williams and Williams Co. 1975), p. 245-270, article entitled "Relevance of Transplantable Animal-tumor Systems to the Selection of New Agents for Clinical Trial".

I claim:

1. A method for inhibiting the growth of malignant cells in a mammal, said cells being susceptible to the action of a compound of the formula

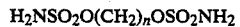

$$H_2NSO_2O(CH_2)_nOSO_2NH_2$$

where n is 6-8, which comprises administering to said mammal an antineoplastically effective amount of said compound incorporated in a suitable pharmaceutically acceptable excipient.

2. A method according to claim 1 wherein said compound is 1,7-heptanediol disulfamate.

3. A method according to claim 1 wherein said compound is 1,6-hexanediol disulfamate.

4. A method according to claim 1 wherein said compound is 1,8-octanediol disulfamate.

5. A method according to claim 1 wherein said malignant cells are those associated with leukemia, mammary tumors, melanoma or colon adenocarcinoma.

6. A method according to claim 5 wherein the compound administered is 1,7-heptanediol disulfamate.

* * * * *